(12) United States Patent
Wagenaar Cacciola et al.

(10) Patent No.: US 9,901,746 B2
(45) Date of Patent: Feb. 27, 2018

(54) SKIN RADIATION APPARATUS AND METHOD

(75) Inventors: Giovanna Wagenaar Cacciola, Eindhoven (NL); Arnd Ritz, Heinsberg (DE); Vincent Stefan David Gielen, Eindhoven (NL); Ian Edward Ashdown, West Vancouver (CA); Damien Loveland, Richmond (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 491 days.

(21) Appl. No.: 13/382,940

(22) PCT Filed: Jun. 23, 2010

(86) PCT No.: PCT/IB2010/052851
§ 371 (c)(1),
(2), (4) Date: Jan. 9, 2012

(87) PCT Pub. No.: WO2011/004285
PCT Pub. Date: Jan. 13, 2011

(65) Prior Publication Data
US 2012/0150264 A1    Jun. 14, 2012

(30) Foreign Application Priority Data
Jul. 9, 2009   (EP) .................................... 09165022

(51) Int. Cl.
| A61N 5/06 | (2006.01) |
| A61N 5/01 | (2006.01) |
| A61B 18/20 | (2006.01) |
| A61B 18/00 | (2006.01) |
| A61N 5/067 | (2006.01) |

(52) U.S. Cl.
CPC ............. *A61N 5/0616* (2013.01); *A61N 5/01* (2013.01); *A61B 18/20* (2013.01); *A61B 2018/00904* (2013.01); *A61B 2018/20351* (2017.05); *A61N 2005/067* (2013.01); *A61N 2005/0637* (2013.01); *A61N 2005/0652* (2013.01); *A61N 2005/0661* (2013.01)

(58) Field of Classification Search
CPC .................... A61B 2018/00452; A61N 5/0616
USPC .......................................................... 606/9
See application file for complete search history.

(56) References Cited

U.S. PATENT DOCUMENTS

| 4,973,848 A | 11/1990 | Kolobanov et al. |
| 6,640,130 B1 | 10/2003 | Freeman et al. |
| 6,879,394 B2 | 4/2005 | Amblard et al. |

(Continued)

FOREIGN PATENT DOCUMENTS

| DE | 102005010723 A1 | 8/2006 |
| EP | 1719541 A1 | 11/2006 |

(Continued)

*Primary Examiner* — John R Downey

(57) ABSTRACT

The present invention relates to a skin radiation apparatus and method. The apparatus includes a photon radiation unit for generating a line-shaped radiation pattern that extends in a first direction; a movement facility for moving the line shaped radiation pattern in a second direction transverse to the first direction; a detection unit for detecting a skin condition profile; and a control unit for controlling the line-shaped radiation pattern, dependent on the detected skin condition profile.

18 Claims, 5 Drawing Sheets

(56) References Cited

U.S. PATENT DOCUMENTS

| | | |
|---|---|---|
| 7,083,611 B2* | 8/2006 | Lemchen ............... 606/9 |
| 7,682,023 B2* | 3/2010 | Van Saarloos ............ 351/209 |
| 2003/0045916 A1 | 3/2003 | Anderson et al. |
| 2005/0143793 A1 | 6/2005 | Korman et al. |
| 2006/0089687 A1 | 4/2006 | Spooner et al. |
| 2006/0111761 A1 | 5/2006 | Butler |
| 2008/0051773 A1 | 2/2008 | Ivanov et al. |
| 2008/0058783 A1* | 3/2008 | Altshuler et al. ............ 606/9 |
| 2009/0174878 A1 | 7/2009 | Wadman |

FOREIGN PATENT DOCUMENTS

| | | |
|---|---|---|
| WO | 0232336 A1 | 4/2002 |
| WO | 2007119202 A1 | 10/2007 |
| WO | 2008041162 A1 | 4/2008 |
| WO | 2008151343 A1 | 12/2008 |

* cited by examiner

SKIN RADIATION APPARATUS AND METHOD

FIELD OF THE INVENTION

The present invention relates to a skin radiation apparatus. The present invention further relates to a skin radiation method.

BACKGROUND OF THE INVENTION

Psoriasis is a chronic, non-infectious inflammatory skin disease characterized by well-demarcated plaques where the cells proliferate quicker than normal (hyperprofileration), leading to a very dry and red skin. The proliferation rate of cells in the epidermis is controlled by the combination of the growth fraction and cell cycle time. In normal skin, the number of cells produced is balanced by the number of cells leaving the epidermal proliferative pool. The time required for a cell to transit between the basal layer and the stratum corneum of the skin (basically from birth to death and getting loose from the skin) is about 4 weeks, while for psoriasis patients, this time is substantially shorter (about 4 days).

Phototherapy has proven an effective treatment of psoriasis. These include broad-band ultraviolet B (UVB) radiation and narrow band UVB, photochemotherapy with psoralen plus ultraviolet A (PUVA), and UV laser. UVB radiation in a wavelength range of 305 to 314 nm has been proven most effective for the treatment of psoriasis.

Devices with PL or TL discharge lamps are known for full body or partial body treatments with narrow band (312 nm) radiation or UVA radiation. These devices do not allow for a specific dose depending on the severity of the plaque itself. Hence, they also irradiate healthy skin. Irradiation of the healthy skin can have negative effects such as ageing or even cancer.

Also handheld applicators are known that emit a narrow beam of radiation, for example from an excimer laser having a wavelength of 308 nm. Such a device allows the medical practitioner to accurately apply the radiation to the affected areas. This can however be an arduous task as the patient's skin may have hundreds or even thousands of mutually isolated affected areas. Furthermore in order for the treatment to be effective it has to be repeated numerous times. Even if the medical practitioner carries out this task in a very concentrated way it can hardly be prevented that certain affected areas are overtreated or remain untreated.

US patent application 2008/0051773 describes an apparatus for treating a skin condition with electromagnetic radiation comprising a source of the electromagnetic radiation and an image-shaping device configured to receive the electromagnetic radiation from the source. The apparatus further comprises a control system configured to cause the image-shaping device to form a shaped treatment image comprising the electromagnetic radiation on a patient's skin based on an image of the skin condition. FIG. 1 of the US patent application shows a camera 102 that captures images of an area 116 of the patient's skin. The control system (a computer 106) identifies psoriatic plaques 120 or other skin conditions to treat, and generates and transmits an appropriate treatment image to the projecting system 104. Ultraviolet light 122 from a laser 108 is focused by the optical system 110 onto an image-shaping device 112. The image-shaping device 112 generates the image from the computer 106 and imparts that image into the light 112 as it reflects it onto the patient's skin 118, through the focusing lens 114, to form a treatment image 124. The camera has a sufficient refresh rate to allow the treatment image to be updated quickly enough to compensate for a patient movement, such as breathing. In some examples the system is fully automated, capable of moving an arm 404 that positions the imaging head 406 to different areas of the patient's body as required.

SUMMARY OF THE INVENTION

It is an object of the present invention to provide an improved skin radiation apparatus.

It is a further object of the present invention to provide an improved skin radiation method.

According to a first aspect of the invention a skin radiation apparatus is provided that comprises:

a photon radiation unit for generating a line-shaped radiation pattern extending in a first direction, the photon radiation unit comprising a photon radiation source, a movement facility for moving the line shaped radiation pattern in a second direction transverse to the first direction, a detection unit for detecting a skin condition profile, a control unit for controlling a power density distribution for the line-shaped radiation pattern dependent on the skin condition profile detected by the detection unit.

A line-shaped radiation pattern is defined herein as a pattern of photon radiation that is restricted to a line shaped area on the surface of the skin to be treated. A line shaped area is understood to be an area having a length that is substantially larger than its width, e.g. at least 10 times as large. The line-shaped radiation pattern does not need to extend over the full length of the line shaped area but may for example radiate one or more portions of the skin within the line shaped area.

A skin condition profile is defined herein as a skin condition as a function of the position on the skin for an entire area or a portion, e.g. a line shaped portion, thereof that is to be treated.

A power density distribution is defined herein as a distribution of the power density (in $mW/cm^2$) within the line shaped radiation pattern as a function of the position in the first direction.

An apparatus according to this first aspect of the invention therefore is suitable for applying radiation with a desired power density distribution in the line-shaped region. Accordingly simple optical means are sufficient and the required power density distribution can be rapidly calculated from the detected skin condition profile for the line-shaped region. Therewith the apparatus can have a relatively low cost in comparison to the known apparatus that requires that a beam is shaped in a complex two-dimensional pattern.

The combination of the control of the power density distribution of the line-shaped radiation pattern in the first direction dependent on the detected skin condition profile on the one hand, and the movement of the line-shaped radiation pattern in the second direction on the other hand, results in a radiation power profile that matches the skin condition profile of the area on the skin to be treated. Therein the radiation power profile is understood to be the two-dimensional distribution of the power density (in $mW/cm^2$) on the surface of the skin that is irradiated.

Dependent on the movement speed and the width of the line shaped radiation pattern, therewith a radiation dose profile is administered to the skin to be treated. The radiation dose profile is defined herein as the two-dimensional distribution of the irradiation dose (in $mJ/cm^2$) applied on the surface of the skin.

In controlling the power density distribution for the line-shaped radiation pattern the control unit may take into account various conditions, such as a maximum power density above which skin damage would occur and a minimum power density below which the treatment has no therapeutic effect. In an embodiment the control unit first calculates a radiation dose that has to be administered in order to improve the skin condition and subsequently controls the power density at a level at which said predetermined radiation dose is administered within a predetermined exposure time.

Hence despite the fact that only simple optical and relatively low computational effort are required an apparatus according to the first aspect of the invention allows automatic treatment of an arbitrary large area of the skin having an arbitrary skin condition profile, due to the combination of the control of the power density distribution of the line-shaped radiation pattern in the first direction with the movement of the line-shaped radiation pattern in the second direction.

The line shaped radiation pattern may be moved for example by moving the photon radiation unit. Alternatively the photon radiation unit may have a controllable radiation deflection device, e.g. a mirror having a controllable orientation. Alternatively it is possible to move the person of which the skin is irradiated with respect to the photon radiation unit. In addition the system may request the patient to move for example by pictorial and/or voice commands.

In an embodiment of the skin radiation apparatus the detection unit is arranged to detect a skin condition in a scan region, and the movement facility is arranged to cause the line-shaped radiation pattern to traverse the scan region. In this embodiment the control unit controls the power density distribution on the basis of the skin condition detected for the scan region.

It is not necessary that the required power density distribution is calculated for the scan region in its entirety before treatment is started. Hence, also in this hybrid arrangement, having a detection unit that detects a skin condition in a two-dimensional scan region and a photon radiation unit that provides a line-shaped radiation pattern, the required power density distribution can be rapidly calculated with simple means.

Dependent on the processing capacity, once the image is captured, the required power density distribution may be calculated for one line at a time or the required power density distribution may be calculated for the entire image or a part of the image before treatment is started. In an embodiment the required power density distribution is calculated for subsequent lines in the same order as the movement direction of the movement facility. Treatment may start with a line in the region for which the power density distribution has already been determined while during treatment the required power density distribution for subsequent positions in the second direction is calculated. The movement facility may transport the photon radiation unit stepwise each time after a line shaped area of the skin is irradiated. Alternatively the photon radiation unit may be moved continuously while irradiating. The apparatus may have an interpolation facility to interpolate the power density distribution for the line-shaped radiation pattern between subsequent positions in the second direction. Interpolation of the power density distribution may be useful if the spatial resolution with which the condition of the skin is sampled is lower than the spatial resolution with which the radiation is administered to the skin. In this case the required power density distribution of the line-shaped radiation pattern, on a skin position in the second direction for which no skin condition was sampled, may be calculated by interpolation from the power density distributions determined for the line-shaped radiation pattern at positions where corresponding skin conditions were sampled. In other words, interpolation is used to determine the power density distribution at discrete positions along the second direction. Interpolation may also be applied if the movement facility causes a continuous movement of the line-shaped radiation pattern. In that case the power density distribution for the line-shaped radiation pattern on the skin may be calculated by interpolation from the power density distributions determined for the line-shaped radiation pattern at neighboring positions with a weighting factor that varies according to said continuous movement. In other words, interpolation is used to determine the power density distribution at successive photon radiation positions in a continuous movement along the second direction. Alternatively, the control unit may stepwise change the power density distribution in the line-shaped radiation pattern each time the movement has proceeded over a predetermined distance in the second direction.

An embodiment of the invention may further comprise a movement detection unit for generating a movement indication signal for the treated skin area, wherein the control unit controls the power density distribution on the basis of the skin condition detected for the scan region and on the basis of the movement indication signal. In this way the patient may freely move while being treated. Movement of the patient may for example be detected and measured by an echo-doppler method.

In another embodiment of the skin radiation apparatus according to the first aspect of the invention the detection unit is arranged to detect a skin condition in a line shaped detection area. This is advantageous in that the detection facility can be relatively cheap. It is also an advantage that only a modest amount of memory is required for storing the skin condition profile for this area.

In a variant of this embodiment the line shaped radiation pattern is mapped to the line shaped detection area and the movement facility is arranged to move the line shaped area to a next position in the second direction only after subsequently the skin condition profile has been determined for the line shaped area and the line-shaped radiation pattern has been applied to said line shaped area. This is advantageous in that only a modest amount of memory space is necessary to store the skin condition data and data indicative for the required power density distribution, as the data indicative for the required power density distribution can be immediately used by the control unit.

In another variant of the last embodiment, the detection unit is arranged to detect a skin condition in a line shaped detection area that is positioned ahead in the second direction with respect to the line shaped radiation area. This is advantageous, as the process of determining the skin condition profile, the process of calculating the power density distribution and the process of generating and applying the line-shaped radiation pattern can take place simultaneously, therewith shortening the total time of the treatment.

The detection unit may be moved independently from the photon radiation unit. However it is advantageous if the detection unit and the photon radiation unit are jointly moved. This simplifies the mechanical requirements of the apparatus. In an embodiment the detection unit and the photon radiation unit are arranged in a common housing that is moved by the movement facility. Movement may take place stepwise or continuously. In case of a continuous movement the control unit may stepwise change the power density distribution within the line-shaped radiation pattern each time the movement has proceeded over a predetermined distance in the second direction. Alternatively the skin radiation apparatus may have an interpolation unit to calculate an interpolated power density distribution that changes substantially continuously with the position in the second direction.

The movement facility may perform a steady movement. However, in an embodiment the control unit further controls the movement facility. The control unit may for example control the movement facility to influence the radiation dose profile (i.e. the energy density in $J/cm^2$). For example, for initial treatment of psoriasis with a relatively low dose, the control unit may cause the movement facility to move at a relatively high speed, while for continuation treatments where a higher dose is required the movement facility be moved at a relatively low speed. Also the control unit may for example increase the movement in the second direction for parts of the skin where no abnormal skin conditions are found.

In addition the control unit may control the movement facility in order to compensate for patient movement in the first direction. This makes it possible to compensate for movements of the patient in the first direction even in case of movements of the patient where the skin area to be treated tends to move outside the line-shaped radiation area. Therewith also "limited length" radiation units may be applied. Thus, the control unit may control the movement facility in the second direction for scanning AND may control the movement facility is the first direction for repositioning.

For relatively small movements of the patient in the first direction, where the skin area to be treated does not tend to move outside the line-shaped radiation area, the movement may alternatively be compensated by recalculation of the power density distribution on the basis of the new position of the patient in the first direction.

An embodiment of the skin treatment apparatus according to the first aspect of the invention further comprises an indication facility for indicating the radiation power profile and or the radiation dose profile as determined by the control unit to be applied at the skin by the moving line-shaped radiation pattern. The indication facility may for example include a projector that is capable of projecting a visible pattern onto the area of the skin to be treated. The visible pattern is preferably isomorphic with the required radiation power profile or the radiation dose profile as determined by the control unit. The pattern is for example dark in skin areas where no therapeutic radiation is scheduled and light in skin areas where a therapeutic radiation is scheduled. The light portions of the pattern may have a brightness which is proportional to the proposed local power density or the proposed local radiation dose. By comparing the pattern projected on the skin with the pattern formed by the skin condition, the medical practitioner can rapidly verify whether the treatment to be applied is correct. Instead of using a visible pattern varying in brightness, alternatively a visible pattern using various colors or a combination thereof is used. In another embodiment the indication facility comprises a display that simultaneously shows an image of the area of the skin to be treated as well as a representation of the radiation power profile and/or the radiation dose profile as scheduled by the control unit. The radiation power profile and/or the radiation dose profile may be represented by a color pattern, a pattern of intensity variations or a combination of both. Alternatively the display may indicate the contours of the spots that are scheduled to be irradiated.

An embodiment of the skin radiation apparatus comprising an indication facility further comprises a feedback facility allowing an operator, such as the medical practitioner to change the radiation power profile scheduled by the control unit. In the embodiment using a projector, the medical practitioner for example gives feedback with an indicator in the form of a pencil capable of communicating its position to the control unit. The indicator for example has a pushbutton that enables the operator to change the radiation power profile and/or the radiation dose profile for said position. The effect of the feedback may be immediately visualized by a change in the pattern projected at the skin to be treated. Instead of communicating the position of the indicator to the control unit, the detection unit for detecting the skin condition may be further arranged to detect the position of the indicator.

In the embodiment using the display, the medical practitioner may indicate at the display how the radiation power profile and/or the radiation dose profile to be applied should be adapted, for example with conventional indication means, such as a mouse, a trackball or a pencil cooperative with a touch sensitive function of the display. The medical practitioner may indicate for example to cancel the treatment of certain spots or indicate spots that should additionally be treated, or the medical practitioner may indicate a change of dose.

An embodiment of the skin treatment apparatus according to the first aspect of the invention further comprises a learning unit for optimizing operation of the detection unit on the basis of the changes in the radiation power profile and/or the radiation dose profile as indicated by the operator. The apparatus may have a selection means allowing the medical practitioner to indicate whether the learning unit should be activated for a particular case or not. For example the learning unit may be activated in case the apparatus is used by an experienced medical practitioner and deactivated when used by less experienced practitioners.

An embodiment of the skin treatment apparatus according to the first aspect of the invention further comprises a storage facility for storing data related to a therapeutic session. The data may comprise an image of the skin captured during the therapeutic session, e.g. at the beginning and or at the end of the session, the applied radiation power profile and/or radiation dose profile, amendments applied in the radiation power profile and/or the radiation dose profile, etc. The stored data may be used to analyze progress achieved with the treatment. The medical practitioner may use this information to control settings of the apparatus. The stored information may also be used as input to the learning unit which may be provided with adaptive learning tools which focus on prior successes and the use of these as the basis for developing future strategies and successes.

An image recognition algorithm may also more rapidly classify the skin condition profile based on classification results obtained from previous sessions.

According to a second aspect of the present invention a skin radiation method is provided comprising,
  detecting a skin condition profile of a person's skin,
  generating a line shaped radiation pattern that extends in a first direction (x),
  moving the line shaped radiation pattern in a second direction (y) transverse to the first direction (x), and dynamically controlling a power density distribution of the line shaped radiation pattern according to the detected skin condition profile.

BRIEF DESCRIPTION OF THE DRAWINGS

These and other aspects are described in more detail with reference to the drawing. Therein.

DETAILED DESCRIPTION OF EMBODIMENTS

Figure 1A:
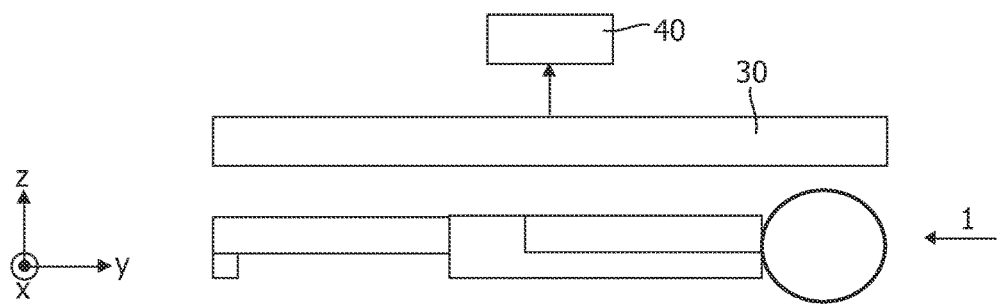
FIG. 1A shows a first part of a skin radiation apparatus according to an embodiment of the invention.

In the following detailed description numerous specific details are set forth in order to provide a thorough understanding of the present invention. However, it will be understood by one skilled in the art that the present invention may be practiced without these specific details. In other instances, well known methods, procedures, and components have not been described in detail so as not to obscure aspects of the present invention.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, and/or sections, these elements, components, and/or sections should not be limited by these terms. These terms are only used to distinguish one element, component and/or section from another element, component, and/or section. Thus, a first element, component, and/or section discussed below could be termed a second element, component, and/or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. All publications, patent applications, patents, and other references mentioned herein are incorporated by reference in their entirety. In case of conflict, the present specification, including definitions, will control. In addition, the materials, methods, and examples are illustrative only and not intended to be limiting.

Figure 1B:
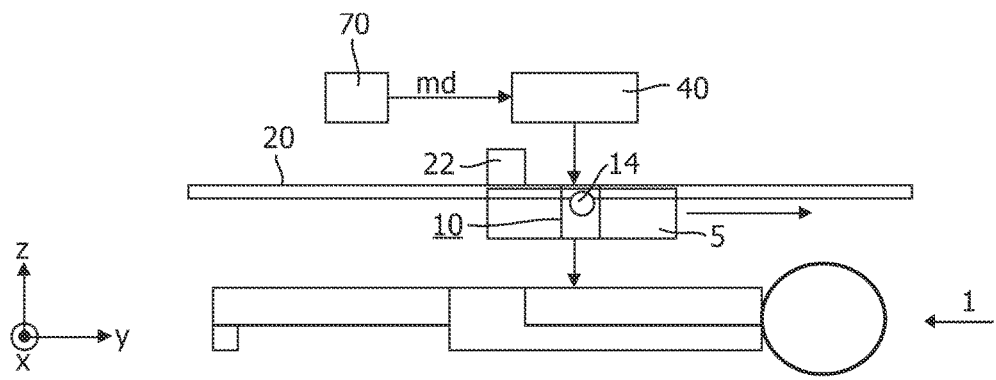
FIG. 1B shows a second part of a skin radiation apparatus according to said embodiment.
Figure 1C:
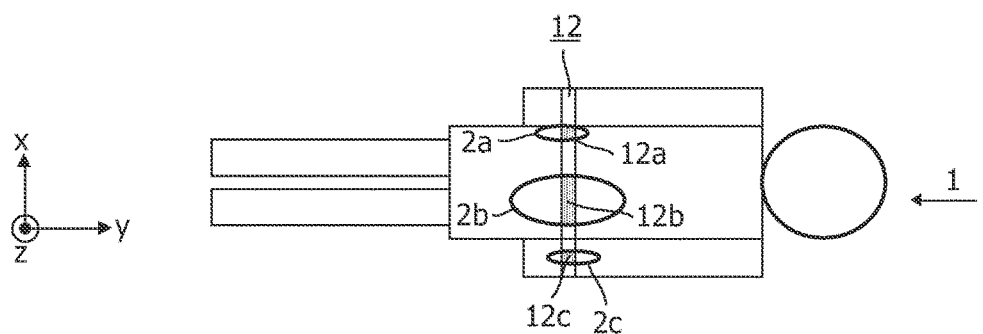
FIG. 1C shows an embodiment of a line shaped radiation pattern irradiated at a person's skin.

FIGS. 1A to 1C show a first embodiment of a skin radiation apparatus. For clarity each of the FIGS. 1A, 1B show a respective part of the skin radiation apparatus. As shown in FIG. 1B, the apparatus comprises a photon radiation unit 10 for generating a line-shaped radiation pattern 12 extending in a first direction x. The photon radiation unit 10, arranged in a housing 5, comprises a photon radiation source 14. In addition the photon radiation unit 10 may comprise optical elements for controlling a beam radiated by the radiation source 14, such as mirrors, lenses, shutters etc. The apparatus further comprises a movement facility 20 for moving the line shaped radiation pattern in a second direction y transverse to the first direction x. The movement facility comprises for example a pair of rails 20 and an actuator 22. During operation the actuator 22 causes the housing 5 with the photon radiation unit 10 to displace in the y-direction along the pair of rails 22. Therewith also the line shaped radiation pattern 12 is displaced in the y-direction. Alternatively the housing may be mounted at a first end of an arm that may be rotated around an axis at its other end. A suitable movement facility is readily available as a state-of-the-art handling robot.

Directions x and y are defined by a plane of the skin that is to be irradiated.

The apparatus further comprises a detection unit 30 (FIG. 1A) for detecting a skin condition profile. In the embodiment shown the detection unit 30 is capable of detecting a skin condition profile for a relatively large region of the skin, e.g. for one side of the body of a patient 1, or for the region formed by the back.

The apparatus further comprises a control unit 40 for controlling a power density distribution for the line-shaped radiation pattern 12 dependent on the skin condition detected by the detection unit 30.

The apparatus may be used in a skin radiation method as follows. First the apparatus detects a skin condition profile of the skin of the patient 1. In this case, as illustrated in FIG. 1A, an image is obtained of the backside of the person in its entirety. Alternatively an image of a more limited portion of the person may be obtained, e.g. the skin of an arm or leg. Subsequently an image processing method is applied to determine the skin condition profile, i.e. the condition of the skin as a function of the spatial location. Methods for obtaining the image and the subsequent image processing methods to determine the skin condition are known as such and are for example described in the co-pending published patent applications WO2008/041162 and WO2007/119202 filed by the same Applicant, as well as in the cited US document. On the basis of the skin condition profile subsequently a radiation power profile is calculated. Although in this embodiment the image of an area of the skin to be treated is taken as a single snapshot, it is not necessary that the required radiation power profile is calculated for this area in its entirety before treatment is started. The required radiation power profile may be calculated for one line shaped area at a time. This allows the required power density profile to be rapidly calculated with simple means. Subsequently, as indicated in FIG. 1B, a moving line shaped area, extending in the x-direction, of the person's skin is radiated with photon radiation. The radiation has a power density distribution that is dynamically controlled according to the skin condition pattern that was detected for said line shaped area. The required radiation power profile for the line shaped area that is irradiated by the line shaped radiation pattern is the power density distribution for said line shaped radiation pattern. FIG. 1C shows by way of example a situation where the line shaped radiation area that is irradiated by the line shaped radiation pattern overlaps three affected regions 2a, 2b, 2c of the skin. Accordingly the line shaped radiation pattern has a relatively high power density in locations 12a, 12b, 12c where it overlaps these affected regions and a relatively low power density (preferably 0) outside these regions. The relation between the skin condition profile and the required radiation dose profile for optimum treatment thereof is known as such. For the healthy skin the radiation dose is preferably as low as possible. For treatment of psoriasis photon radiation doses may be used dependent on the skin type and the stage of the treatment. Generally speaking the therapy is started with a relatively low dose and in subsequent therapeutic sessions the dose is gradually incremented to a final, maximum value. This is indicated in more detail in the following table Table 1. Therein the first column indicates the skin type, the second column indicates the required starting dose for the first treatment, the third column indicates the value with which the dose is incremented at each therapeutic session and the last column indicates the maximum dose.

TABLE 1

Recommended photon radiation dose for treatment of psoriasis

| Skin type | Starting dose (mJ/cm$^2$) | Increment (mJ/cm$^2$) | Final (mJ/cm$^2$) |
| --- | --- | --- | --- |
| 1 | 300 | 100 | 2000 |
| 2 | 300 | 100 | 2000 |
| 3 | 500 | 100 | 2000 |
| 4 | 500 | 100 | 2000 |
| 5 | 800 | 150 | 5000 |
| 6 | 800 | 150 | 5000 |

Depending on the circumstances a choice may be made whether the dose is to be provided in the form of a relatively short irradiation with a relatively high power density (e.g. for professional applications) or a relatively long irradiation with a relatively low power density (e.g. for home applications). For example, for a skin radiation apparatus for use at home it may be preferred to apply a relatively low power density. An apparatus for consumer applications may for example provide a line-shaped radiation pattern with a maximum power density of 10 mW/cm$^2$ and may apply a dose of 300 mJ/cm$^2$ in 30 s. For professional use by medically trained practitioners a line shaped radiation pattern having a significantly higher maximum power density may be applied allowing for a faster treatment, e.g. 50 mW/cm$^2$ during 6 s or 300 mW/cm$^2$ during 1 s.

Irradiation with a particular duration may be achieved by a stepwise scanning of the area of the skin to be treated. For example the line shaped radiation pattern is stepwise displaced in the second direction with a stepsize s equal to the width of the radiation pattern each time the required radiation dose is reached. It is not necessary that the step size s with which the line shaped radiation pattern is displaced is equal to the width w of the pattern. The step size s may for example be a fraction of the width w, e.g. equal to half the width w. In this way a spatially relatively uniform radiation dose is reached also if the power density distribution in the second direction is relatively non-uniform, e.g. bell-shaped. When stepping with a step-size s each time interval $t_s$, an average scanning speed $v_s$ equal to $s/t_s$ is obtained. It is not necessary that the required dose for a particular treatment session is applied in a single scan. Alternatively an accumulated dose may be obtained after a plurality of scans in a session, therewith enabling an intermittent application of radiation. This gives the medical practitioner more freedom in treatment algorithms. For example a dose of 300 mJ/cm$^2$ is reached with 3 scans at a power density of 100 mW/cm$^2$ and an exposure time of 1 s each.

Instead of scanning step-wise, the line-shaped radiation pattern may be moved continuously with a velocity $v_c$. In this case the average exposure time $t_{exp}$ is $w/v_c$.

The selection of the width w depends on the requirements of spatial accuracy with which the dose is to be controlled as well as the speed of treatment. A large width w is favorable for a fast treatment, however at the cost of a lower accuracy with respect to the spatial resolution. For practical purposes the width of the line shaped radiation pattern is for example in the range of 0.1 cm to 2 cm. If the width is larger than 2 cm, the spatial resolution with which the radiation can be applied to the surface of the skin becomes too low. A width smaller than 0.1 cm, although possible, would require relatively expensive optical means while not resulting in a more accurate treatment. Moreover, a small width would either require a relatively high power density, which may be dangerous in case of failure of the movement facility, or would result in long treatment times in case a lower power density is applied.

It is noted that the dose to be applied may further be dependent on the severity of the skin disease.

The embodiment of the apparatus shown in FIGS. 1A and 1B further comprises a movement detection unit 70 for generating a movement indication signal md, wherein the control unit 40 controls the power density distribution on the basis of the skin condition detected for the region and on the basis of the movement indication signal md. In this way the patient may move a bit while being treated. The movement detection unit 70 comprises for example an echo-doppler detector.

Figure 2A:
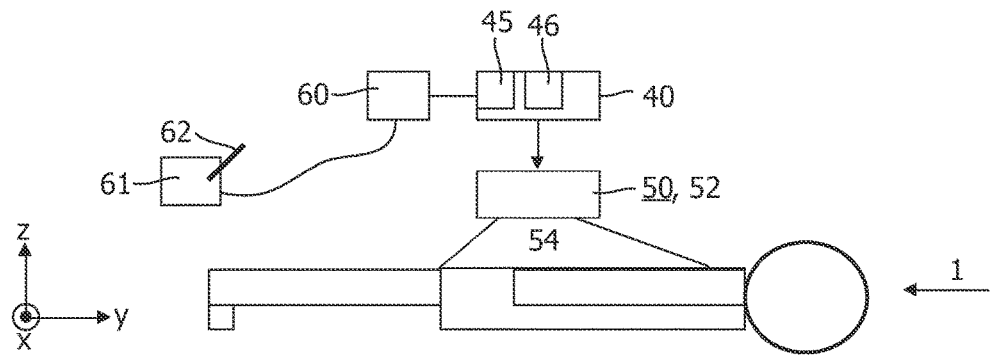
FIG. 2A shows a skin radiation apparatus according to a further embodiment of the invention.
Figure 2B:
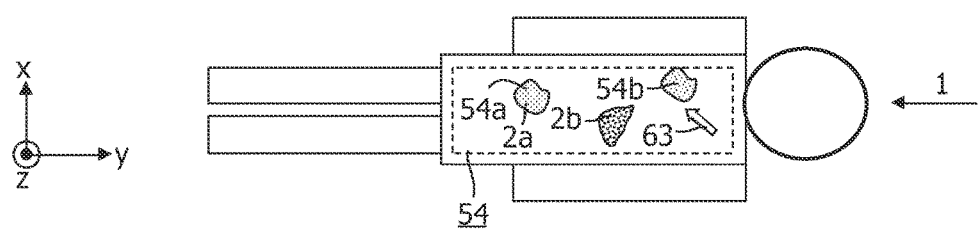
FIG. 2B shows an embodiment of a pattern projected by a part of the skin radiation apparatus.

FIGS. 2A and 2B shows an embodiment of the skin radiation apparatus that comprises an indication facility 50 for indicating the radiation power profile and/or the radiation dose profile of the radiation to be applied, as determined by the control unit, at the skin by means of moving a line-shaped radiation pattern. In the embodiment shown the indication facility 50 comprises a projector 52 that is capable of mapping a visible pattern 54 at the area of the skin to be treated. The visible pattern 54 is isomorphic with the required radiation power profile and/or the radiation dose profile as determined by the control unit 40. In the example shown in FIG. 2B, the patient 1 has two isolated regions 2a, 2b affected by psoriasis. It is noted that in practice the number of isolated regions may be significantly higher, e.g. hundreds to thousands of isolated affected regions may be formed on the skin. In the example shown the projected pattern 54 comprises two illuminated areas 54a, 54b that indicate the areas where the control unit 40 schedules radiation of the skin with therapeutic radiation. In this example the medical practitioner will observe that the illuminated area 54a coincides with the region 2a affected by psoriasis. However the practitioner also observes that one affected region 2b is not highlighted in the visible pattern. In this case the practitioner may apply a correction for example by indicating the contour of the affected region 2b with a pointing device and by giving a command to the controller 40 that this region should also be treated. To this end the controller 40 is coupled to a user interface 60 that serves as a feedback facility. The user interface 60 may comprise any means that is suitable to exchange information between the controller 40 and the practitioner, including for example a keyboard, a mouse, voice control, touch screen, dedicated control buttons, etc. The practitioner will also observe that the projected pattern 54 comprises a highlighted area 54b that is not affected by psoriasis. The practitioner may now point within this highlighted area 54b and give a command to the controller 40 that this area should not be treated. To indicate a position in a certain area, the user interface may for example comprise a tablet 61 and a pencil 62. The position indicated by the practitioner may be indicated by an arrow 63 that is projected onto the skin by the projection means 52. The practitioner may also indicate that the shape or power density or the dose of a highlighted area should be modified. The pattern 54 may be edited in way analogous to the way an image is "photoshopped". In response to the commands given by the practitioner, the control unit 40 modifies the projected pattern 54 to indicate or to reflect the resulting radiation power profile or radiation power dose to be applied to the area to be treated.

The apparatus shown in FIG. 2A, further comprises a learning unit 45 for teaching optimal operation of the detection unit 30 or controller 40, or both, on the basis of the proposed amendments to the radiation power profile and/or the radiation dose profile indicated by the operator/practitioner. The learning unit 45 may have means for selective activation. For example a password may be needed to restrict activation to experienced practitioners.

Figure 2C:
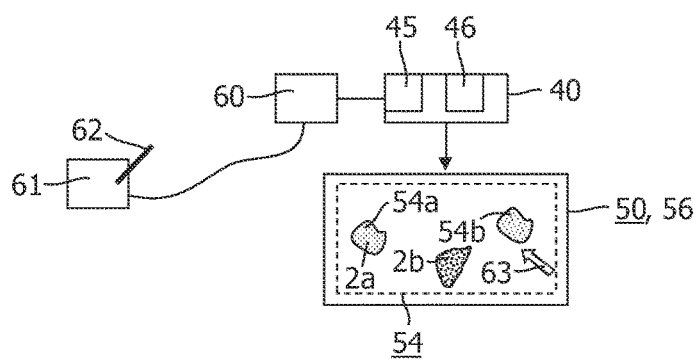
FIG. 2C shows a skin radiation apparatus according to a further embodiment of the invention.

FIG. 2C shows another embodiment, wherein the indication facility 50 comprises a display 56 that simultaneously shows an image of the area of the skin to be treated as well as a representation of the proposed radiation power distribution or the radiation dose distribution, e.g. by a color pattern, a pattern of intensity variations or a combination of both. Alternatively the display 56 may indicate the contours of the spots that are scheduled to be irradiated. The medical practitioner may indicate proposed amendments to the treatment in a way similar to that described with reference to FIGS. 2A and 2B. The practitioner may control various settings, e.g. the brightness and contrast with which the image of the area of the skin is displayed independent of the brightness and contrast with which the pattern 54 is displayed to obtain optimum visibility. Preferred settings may be stored, e.g. as default values. The display 56 may be a touch screen, so that the practitioner may indicate proposed amendments directly by pointing at the display 56.

The skin radiation apparatus as shown in FIGS. 2A to 2C further comprises a storage facility 46 for storing data related to a therapeutic session. The data may comprise an image of the skin captured at the therapeutic session, e.g. at the beginning and/or at the end of the session, the applied radiation power profile, the applied radiation dose profile, amendments applied in the radiation power profile and/or the radiation dose profile etc. Data from multiple sessions related to a complete treatment program may be stored. The stored data may be used to analyze progress achieved with the treatment. The medical practitioner may use this information to control settings of the apparatus. An image recognition algorithm may also more rapidly classify the condition of the skin based on results obtained from previous sessions. In an embodiment the classification of skin conditions is based on a comparison of the results from the captured image of the skin with information from a database provided with the system. This database comprises e.g. data on the color appearance of skin in different states of inflammation. The storage facility 46 may be any non-volatile storage facility, such as a flash-memory or a hard-disk. Also a volatile storage facility could be used, but in the latter case a reliable permanently available power source is necessary. The system may comprise a network connection for consulting data, e.g. skin condition classification data, on remote data storage devices or knowledge databases.

Figure 3A:
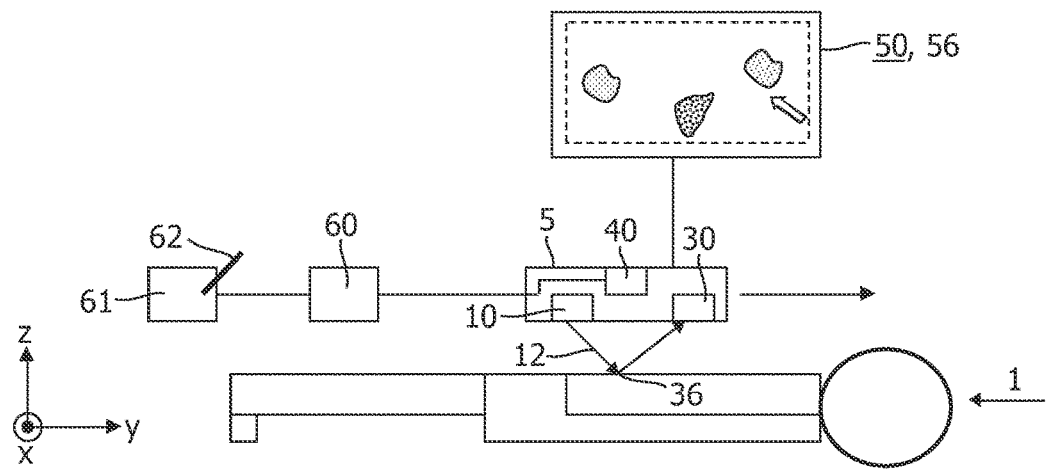
FIG. 3A shows a first view of a skin radiation apparatus according to a still further embodiment of the invention.
Figure 3B:
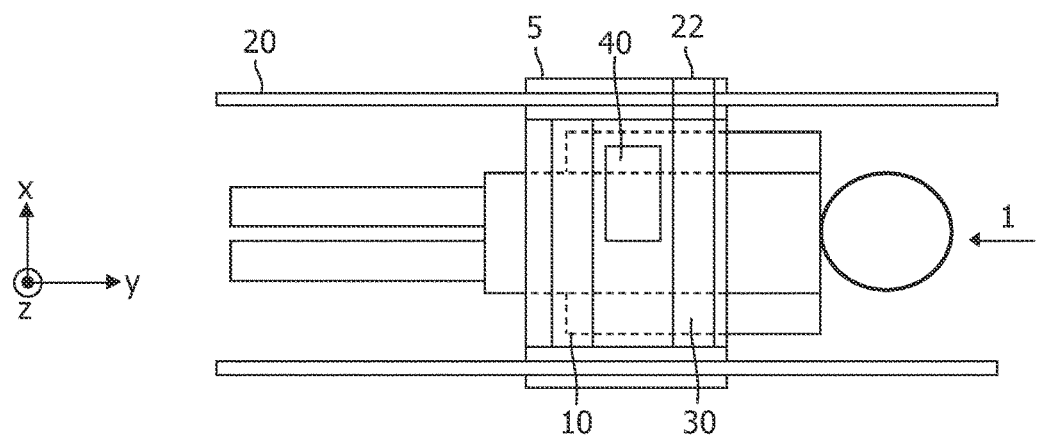
FIG. 3B shows a second view of a skin radiation apparatus according to a still further embodiment of the invention, FIG. 4A schematically shows a skin radiation apparatus according to a still further embodiment of the invention.

FIGS. 3A and 3B show an embodiment of the radiation apparatus wherein the detection unit 30, the photon radiation unit 10 and also the controller 40 are mounted in a common housing 5 that is movable by the movement facility 20, 22. The detection unit 30 is arranged to detect a skin condition in a line shaped area 36. Accordingly a full-fledged camera for imaging the skin to be treated is superfluous. Instead a linear camera, such as a CCD-camera can be used. It is also an advantage that only a modest amount of memory is required for storing the data indicative for the skin condition. In the embodiment shown the line shaped radiation pattern 12 is directed at the line shaped area 36. The movement facility 20, 22 is arranged to move the line shaped area 36 to a next position in the second direction y after subsequently the skin condition profile has been determined and the line-shaped radiation pattern has been applied to the line shaped area 36. In this way only a modest amount of memory space is necessary to store the skin condition profile and data indicative for the required radiation power profile, as this data can be immediately used by the control unit 40 for controlling the power density distribution of the line shaped radiation pattern.

In case the medical practitioner first desires to observe the proposed radiation power profile and/or the radiation dose profile, the apparatus may make a full scan over the area to be treated and gather the required information about the skin condition of the patient, as well as the proposed treatment. Subsequently thereto the results may be shown on a display 56, e.g. a touch screen, and the medical practitioner may be enabled to amend the proposed radiation power profile and/or radiation dose profile by feedback means 60, 61, 62, in the same way as described with reference to the embodiment of FIG. 2C. During this full scan the photon radiation unit 10 may be disabled. The radiation power profile and/or radiation dose profile may be stored, so that for a subsequent treatment the medical practitioner can rapidly verify whether the radiation power profile and/or radiation dose profile to be applied are still suitable. Alternatively, when the detection unit 30 is capable of detecting the skin condition with sufficient reliability, feedback means and a display 50 may be superfluous. Accordingly in an embodiment the skin radiation apparatus does not have a feed-back facility and or an indication facility.

Figure 4A:
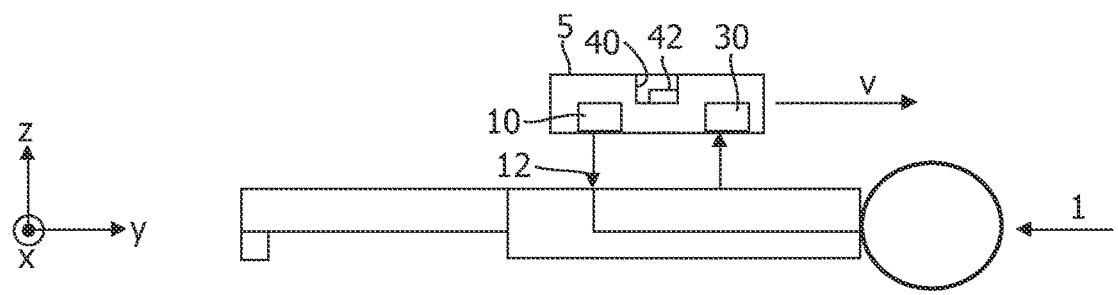
FIG. 4B shows an aspect relating to a use of the skin radiation apparatus of FIG. 4A, FIG. 5A schematically shows an embodiment of a radiation source in an embodiment of the skin-radiation apparatus, FIG. 5B schematically shows an embodiment of a radiation source in another embodiment of the skin-radiation apparatus, FIG. 5C schematically shows an embodiment of a radiation source in again another embodiment of the skin-radiation apparatus.
Figure 4B:
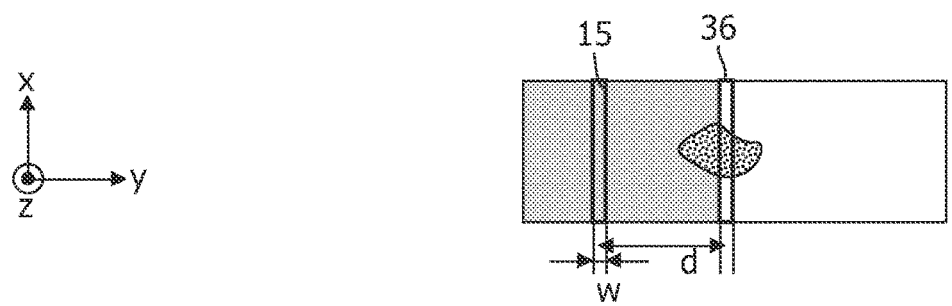

FIGS. 4A to 4B shows a further embodiment. The apparatus according to this embodiment of the invention starts treatment with application of the line shaped radiation pattern 12 in a line shaped area 15 in the region for which the radiation power profile has already been determined, while the required radiation power profile is calculated for a subsequent positions 36 (FIG. 4B) in the second direction y. The movement facility (not shown) transports the housing 5 with the photon radiation unit 10 stepwise each time after a line shaped area 15 of the skin is irradiated. Therewith also the detection unit 30, arranged in the same housing 5 is transported to a next position. Alternatively, in another embodiment of the radiation apparatus the line shaped areas 15 and 36 may be adjacent areas wherein, during operation a first (first in the direction of movement by the moving facility, i.e. the second direction) line shaped area 36 is measured to determine the a skin condition profile while a second (subsequent to the first in the direction of movement by the moving facility, i.e. the second direction) line shaped area 15 is radiated with a power density distribution radiation pattern. After moving the movement facility in the second direction with an increment of one line shaped area width, a new first line shaped area 36 is presented for skin condition profile determination while the previous first line shaped area 36 now becomes the new second line shaped area 15 for photon radiation, and the previous second line shape area 15 has finished the photon radiation. These embodiments may operate faster than the embodiment described with FIGS. 3A and 3B because at least some of the steps related skin condition determination, radiation power density calculation and applying the photon radiation may be executed concurrently instead of sequentially.

It is not necessary that the housing 5 with the photon radiation unit 10 is moved stepwise. Alternatively the photon radiation unit 10 may be moved continuously while irradiating. The apparatus may have an interpolation facility 42 to interpolate the power density distribution for the line-shaped radiation pattern 12 between subsequent positions in the second direction y. Alternatively, the control unit 40 may stepwise change the power density distribution in the line-shaped radiation pattern each time the movement has proceeded over a predetermined distance in the second direction y.

The administered photon radiation dose is proportional to the line width w divided by the movement speed v. This is either the continuous speed or the average speed resulting from the stepping process, which is $s/t_s$, wherein s is the step-size and $t_s$ is the time interval between subsequent steps.

The available time for detecting the skin condition and calculating the required radiation power profile is d/v, wherein d is the distance between the line shaped region 36 for which the skin condition is detected and the line shaped region 15 that is treated with radiation.

Figure 5A:
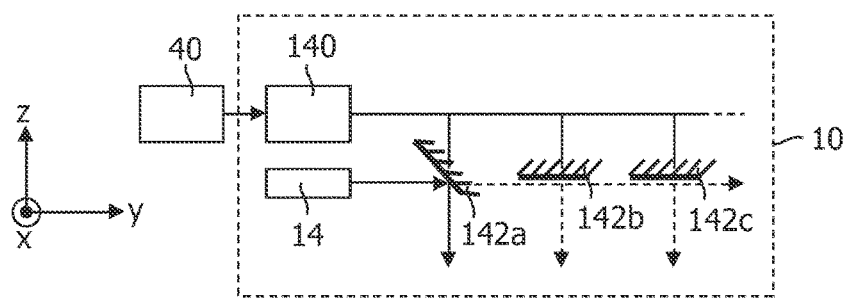
Figure 5B:
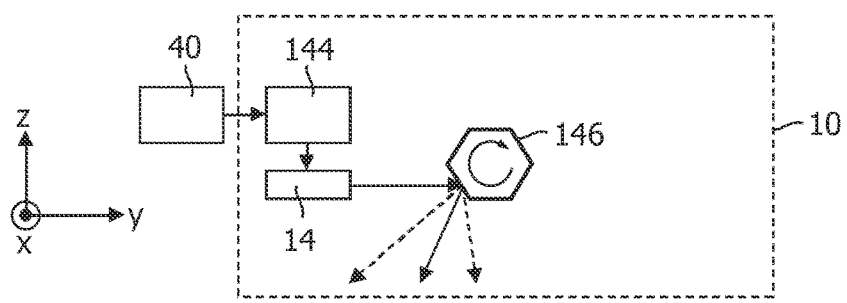
Figure 5C:
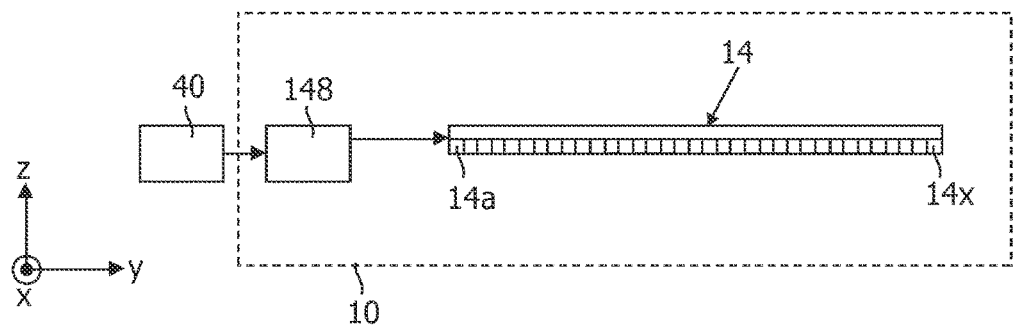

FIGS. 5A to 5C shows photon radiation units 10 for various embodiments of the apparatus. In the embodiment shown in FIG. 5A, the radiation source 14 is a laser, for example an excimer laser having a wavelength of 308 nm. The photon radiation unit 10 comprises apart from the radiation source 14, a plurality of rotatable mirrors 142a to 142c. Although only 3 rotatable mirrors are shown for clarity, in practice a substantially larger amount of mirrors may be used. The photon radiation unit 10 further comprises a driver 140 that controls the plurality of rotatable mirrors 142a,b,c. The rotatable mirrors 142a,b,c are controllable in a first orientation (as shown for mirror 142a) wherein they reflect photon radiation from the photon radiation source 14 towards the line shaped area and a second orientation (as shown for mirrors 142b, c) wherein the photon radiation can pass along the mirror. A desired radiation dose distribution within the line shaped region can be obtained by subsequently rotating the mirrors in the first orientation for a time proportional to the desired radiation dose. Alternatively the radiation power and therewith the radiation dose may be controlled by regulating the power of the laser 14. These two ways of control may be combined.

FIG. 5B shows a second embodiment, wherein the power of the laser 14 is modulated by a laser driver 144, controlled by the controller 40. The laser beam emitted by the laser 14 is directed towards a rotating hexagonal mirror 146, that reflects the radiation of the laser 14 towards a position within the line shaped area 12 that is to be irradiated.

In the embodiment of FIG. 5C, the photon radiation source 14 comprises a plurality of radiation source elements 14a, . . . , 14x, such as for example light emitting diodes (LED), that are each capable of radiating a respective portion within the line shape area of the skin. The photon radiation source 14 is controlled by a driver 148 that is on its turn controlled by the controller 40.

Arithmetical and logical operations carried out by various parts of the apparatus of the control unit 40, by the detection unit 30, and the drivers 140, 144 or 148 may be carried out by dedicated hardware, by software in a programmable processors or by a combination of both.

Although the apparatus and method described above have been described particularly with reference to the treatment of psoriasis, the apparatus and method can alternatively be modified to be suitable for the recognition and treatment of other skin conditions, such as myocosis fungoides, eczema, actinic keratosis, lichen planus etc. For treatment of other skin conditions than psoriasis, other photon radiation wavelengths, wavelength ranges or combinations may be used.

In the claims the word "comprising" does not exclude other elements or steps, and the indefinite article "a" or "an" does not exclude a plurality. A single component or other unit may fulfill the functions of several items recited in the claims.

The mere fact that certain measures are recited in mutually different claims does not indicate that a combination of these measures cannot be used to advantage. Any reference signs in the claims should not be construed as limiting the scope. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The invention claimed is:

1. A skin radiation apparatus comprising:
   a photon radiation emitter configured to generate a line-shaped radiation pattern extending in a first direction, the photon radiation emitter comprising a photon radiation source having a plurality of elements, each configured to simultaneously generate a respective portion of the line-shaped pattern, wherein the line-shaped radiation pattern is generated without requiring any movement of the photon radiation emitter,
   a movement facility configured to cause movement of the line-shaped radiation pattern in a second direction transverse to the first direction,
   a skin condition detector configured to detect a skin condition profile,
   a controller configured to determine a power density distribution for the line-shaped radiation pattern, that simultaneously has multiple different positive power densities, and is dependent on: the skin condition profile detected by the skin condition detector, a maximum power density above which skin damage would occur, and a minimum power density below which the treatment has no therapeutic effect, the controller being further configured to control the photon radiation emitter to generate the determined power density distribution of the line-shaped radiation pattern having the multiple different positive power densities along the first direction.

2. The skin radiation apparatus of claim 1, wherein the skin condition detector is configured to detect a skin condition profile in a scan region, and wherein the movement facility is configured to cause the line-shaped radiation pattern to traverse the scan region and wherein the controller controls the power density distribution depending on the skin condition profile detected for the scan region.

3. The skin radiation apparatus of claim 2, wherein the line-shaped radiation pattern is applied to a person's skin, the skin radiation apparatus comprising:
movement detector configured to detect any movement of the person not caused by the movement facility, and generate a corresponding movement indication signal, wherein the controller is configured to control the power density distribution based on the skin condition profile detected for the scan region and on the basis of the movement indication signal.

4. The skin radiation apparatus of claim 1, wherein the skin condition detector is configured to detect a skin condition profile in a line-shaped detection area.

5. The skin radiation apparatus of claim 4, wherein the line-shaped radiation pattern is targeted at the line-shaped detection area and wherein the movement facility is configured to move the line-shaped detection area to a next position in the second direction after the skin condition profile in the line-shaped detection area has been determined and the line shaped radiation pattern has been applied to the line-shaped detection area.

6. The skin radiation apparatus of claim 4, wherein the skin condition detector is configured to detect a skin condition in a further line-shaped detection area that is positioned ahead in the second direction with respect to a line-shaped radiation area that is irradiated by the line-shaped radiation pattern.

7. The skin radiation apparatus of claim 4, wherein the skin condition detector and the photon radiation emitter are arranged in a common housing that is moved by the movement facility.

8. The skin radiation apparatus of claim 1, further comprising an indication facility for indicating at least one of: a radiation power profile, and a radiation dose profile, scheduled by the controller to be applied at the skin.

9. The skin radiation apparatus of claim 8, further comprising a feedback facility allowing an operator to change at least one of the radiation power profile and the radiation dose profile as scheduled by the controller.

10. The skin radiation apparatus of claim 9, comprising a learning unit for teaching optimal operation of the skin condition detector or controller on the basis of the changes to the radiation power profile and/or the radiation dose profile as indicated by the operator.

11. The skin radiation apparatus of claim 1, comprising a storage facility for storing data related to a therapeutic session.

12. A skin radiation method comprising the acts of:
in a skin radiation apparatus:
detecting via a skin condition sensor, a skin condition profile of a person's skin,
generating via a photon radiation emitter, a line-shaped radiation pattern that extends in a first direction, wherein the generating act comprises utilizing a photon radiation source having a plurality of elements, each element capable of simultaneously providing a respective portion of the line-shaped pattern, wherein the line-shaped radiation pattern is generated without requiring any movement of the photon radiation emitter,
moving by a movement facility, the line-shaped radiation pattern in a second direction transverse to the first direction, and
controlling via a controller, the photon radiation emitter to generate a power density distribution of the line-shaped radiation pattern having multiple different positive power densities along the first direction based on the detected skin condition profile,
a maximum power density above which skin damage would occur, and a minimum power density below which the treatment has no therapeutic effect.

13. The skin radiation method of claim 12, further comprising an act of generating a visible pattern that is isomorphic to at least one of: a scheduled radiation power profile, and a scheduled radiation dose profile, after the skin condition profile is scheduled and before generating the line-shaped radiation pattern.

14. The skin radiation method of claim 13, further comprising an act of changing at least one of: the scheduled radiation power profile, and the scheduled radiation dose profile, upon commands received by the controller from an operator, after generating the visible pattern.

15. The skin radiation method of claim 14, comprising an optimizing operation of the detecting of the skin condition profile, the optimizing operation based on the changes to at least one of: the radiation power profile, and the radiation dose profile, as indicated by the received commands.

16. The skin radiation method of claim 14, comprising an optimizing operation of the generating the line-shaped radiation pattern based on the changes to at least one of: the radiation power profile, and the radiation dose profile, as indicated by the received commands.

17. A skin radiation apparatus comprising:
a photon radiation emitter configured to generate a line-shaped radiation pattern extending in a first direction, the photon radiation emitter comprising a photon radiation source having a plurality of radiation source elements, wherein in use, the plurality of the radiation source elements simultaneously provide respective portions of the line-shaped pattern,
a movement facility configured to cause movement of the line-shaped radiation pattern in a second direction transverse to the first direction,
a skin condition detector configured to detect a skin condition profile,
a controller configured to determine a power density distribution for the line-shaped radiation pattern, that simultaneously has at least three different power densities, and is dependent on: the skin condition profile detected by the skin condition detector, a maximum power density above which skin damage would occur, and a minimum power density below which the treatment has no therapeutic effect, the controller being further configured to control the photon radiation emitter to generate the determined power density distribution of the line-shaped radiation pattern having multiple different positive power densities along the first direction.

18. A computer-readable storage-medium that is not a transitory propagating signal or wave, the medium modified by control information including instructions for performing a method for irradiating skin, the method comprising:

in a skin irradiation apparatus:
detecting via a skin condition sensor, a skin condition profile of a person's skin,
generating via a photon radiation emitter, a line-shaped radiation pattern that extends in a first direction, wherein the generating step comprises utilizing a photon radiation source having a plurality of elements, each element capable of simultaneously providing a respective portion of the line-shaped pattern, wherein the line-shaped radiation pattern is generated without requiring any movement of the photon radiation emitter,
moving by a moving facility, the line-shaped radiation pattern in a second direction transverse to the first direction, and
controlling via a controller, the photon radiation emitter to generate a power density distribution of the line-shaped radiation pattern having multiple different positive power densities along the first direction based on the detected skin condition profile,
a maximum power density above which skin damage would occur, and a minimum power density below which the treatment has no therapeutic effect.

* * * * *